(12) United States Patent
Karlson et al.

(10) Patent No.: US 8,926,943 B2
(45) Date of Patent: Jan. 6, 2015

(54) ISOTOPE PREPARATION METHOD

(75) Inventors: Jan Roger Karlson, Oslo (NO); Peer Børretzen, Nærsnes (NO)

(73) Assignee: Algeta ASA, Oslo (NO)

( * ) Notice: Subject to any disclaimer, the term of this patent is extended or adjusted under 35 U.S.C. 154(b) by 0 days.

(21) Appl. No.: 13/695,353

(22) PCT Filed: Apr. 29, 2011

(86) PCT No.: PCT/EP2011/002155
§ 371 (c)(1),
(2), (4) Date: Jan. 3, 2013

(87) PCT Pub. No.: WO2011/134671
PCT Pub. Date: Nov. 3, 2011

(65) Prior Publication Data
US 2013/0136690 A1 May 30, 2013

(30) Foreign Application Priority Data
Apr. 30, 2010 (GB) .................................. 1007354.2

(51) Int. Cl.
| A61K 51/00 | (2006.01) |
| A61K 51/02 | (2006.01) |
| C01F 13/00 | (2006.01) |
| A61K 51/12 | (2006.01) |
| G21G 1/00 | (2006.01) |

(52) U.S. Cl.
CPC ............. C01F 13/00 (2013.01); A61K 51/1282 (2013.01); G21G 1/0005 (2013.01); A61K 51/00 (2013.01); G21G 2001/0094 (2013.01)
USPC ....... 424/1.11; 424/1.25; 424/1.41; 424/1.69; 424/1.73

(58) Field of Classification Search
USPC ................ 424/1, 1.11, 1.21, 1.25, 1.41, 1.49, 424/1.53, 1.69, 1.73, 9, 12; 423/2
See application file for complete search history.

(56) References Cited

U.S. PATENT DOCUMENTS

| 4,390,517 | A * | 6/1983 | O'Brien et al. .............. 424/1.45 |
| 5,809,394 | A | 9/1998 | Bray et al. |
| 5,885,465 | A | 3/1999 | Bray et al. |
| 6,635,234 | B1 | 10/2003 | Larsen et al. |
| 7,553,461 | B2 | 6/2009 | Horwitz et al. |
| 2003/0206857 | A1 | 11/2003 | Larsen et al. |
| 2007/0009409 | A1 * | 1/2007 | Gali et al. .......................... 423/2 |
| 2007/0131618 | A1 | 6/2007 | Horwitz et al. |

OTHER PUBLICATIONS

L.I. Guseva et al. Anion-Exchange Separation of Radium from Alkaline-Earth Metal and Actinides in Aqueous-Methanol Solution of HNO3, 227Ac-223Ra Generator, Radiochemistry, vol. 46(1), 58-62, 2004.*

Howell et al., "Radiotoxicity of Gadolinium-148 and Radium-223 in Mouse Testes: Relative Biological Effectiveness of Alpha-Particle Emitters In Vivo," *Radiation Research* 147: 342-348 (1997).

International Search Report for PCT/EP2011/002155, mailed Jul. 25, 2011 (4 pages).

Written Opinion of the International Searching Authority for PCT/EP2011/002155, mailed Jul. 25, 2011 (4 pages).

Zielinska et al., "An improved method for the production of Ac-225/Bi-213 from Th-229 for targeted alpha therapy," Solvent Extraction and Ion Exchange. 25:339-49 (2007).

Office Action for U.S. Appl. No. 13/695,355, dated Oct. 31, 2013 (9 pages).

First Examination Report for New Zealand Patent Application No. 700258, dated Oct. 10, 2014 (2 pages).

Henriksen et al., "223Ra for endoradiotherapeutic applications prepared from an immobilized 227Ac/227Th source," Radiochimica Acta 89:661-666 (2001).

* cited by examiner

*Primary Examiner* — Michael G Hartley
*Assistant Examiner* — Jagadishwar Samala
(74) *Attorney, Agent, or Firm* — Clark & Elbing LLP

(57) ABSTRACT

The present invention provides a method for the generation of $^{223}Ra$ of pharmaceutically tolerable purity comprising i) preparing a generator mixture comprising $^{227}Ac$, $^{227}Th$ and $^{223}Ra$; ii) loading said generator mixture onto a strong base anion exchange resin; iii) eluting said $^{223}Ra$ from said strong base anion exchange resin using a first mineral acid in an alcoholic aqueous solution to give a first eluted $^{223}Ra$ solution; iv) loading the $^{223}Ra$ of the first eluted $^{223}Ra$ solution onto a strong acid cation exchange resin; and v) eluting the $^{223}Ra$ from said strong acid cation exchange resin using a second mineral acid in aqueous solution to provide a second eluted solution. The invention additionally provides products of corresponding purity and/or products obtained or obtainable by such a method.

27 Claims, 5 Drawing Sheets

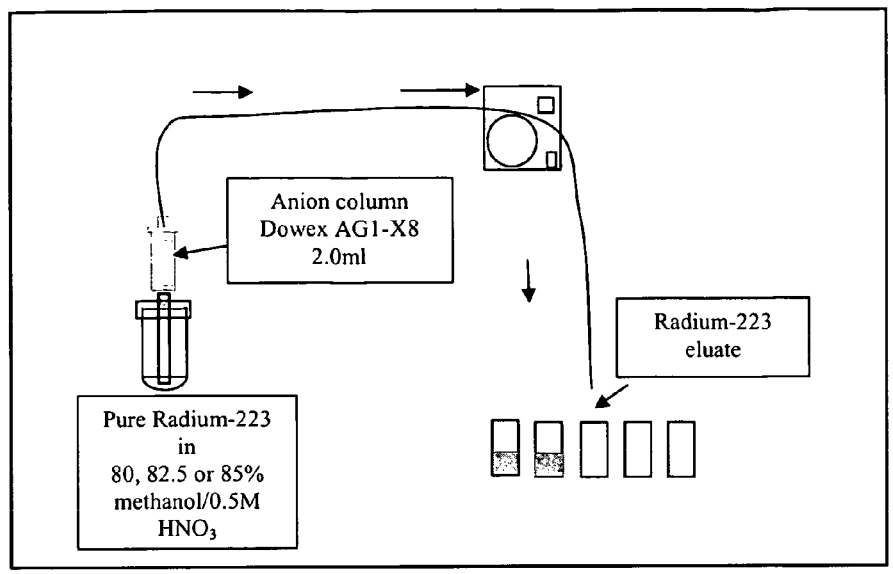
Figure 1 - set up to determine radium-223 yield on a 2ml anion column.
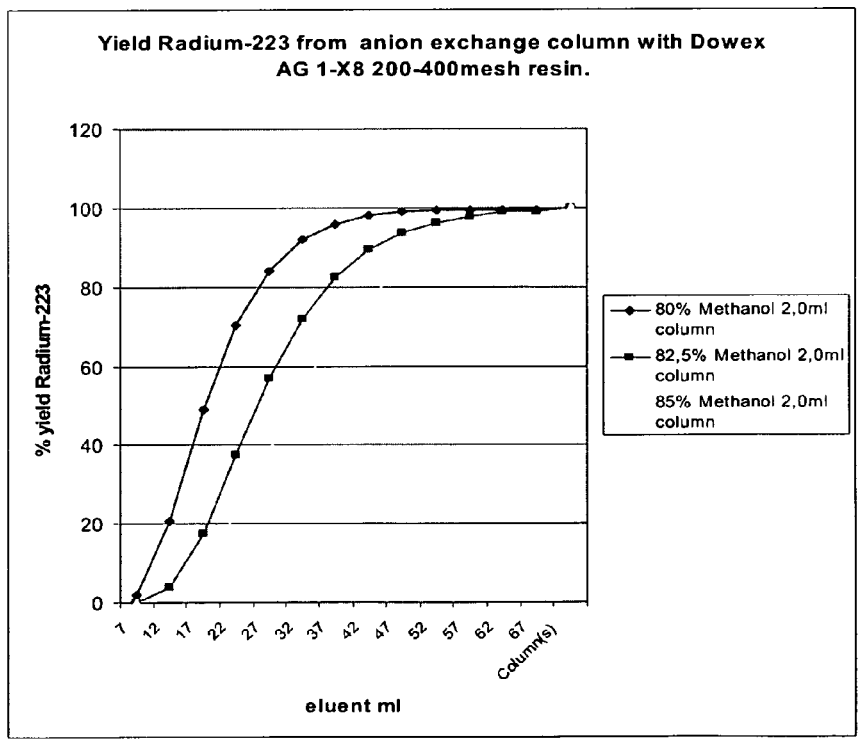
Figure 2 - elution profile of radium-223 from a 2ml anion-exchange column packed with AG 1-X8 200-400mesh particles

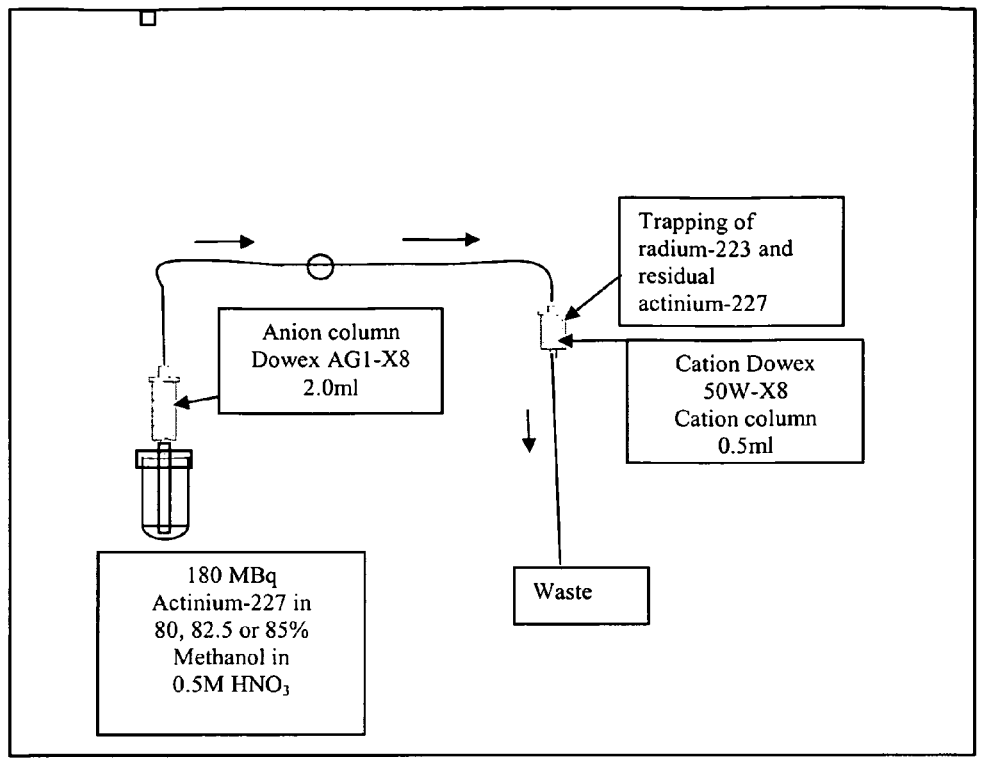
Figure 3 - setup for evaluating leakage of actinium-227 from anion columns.
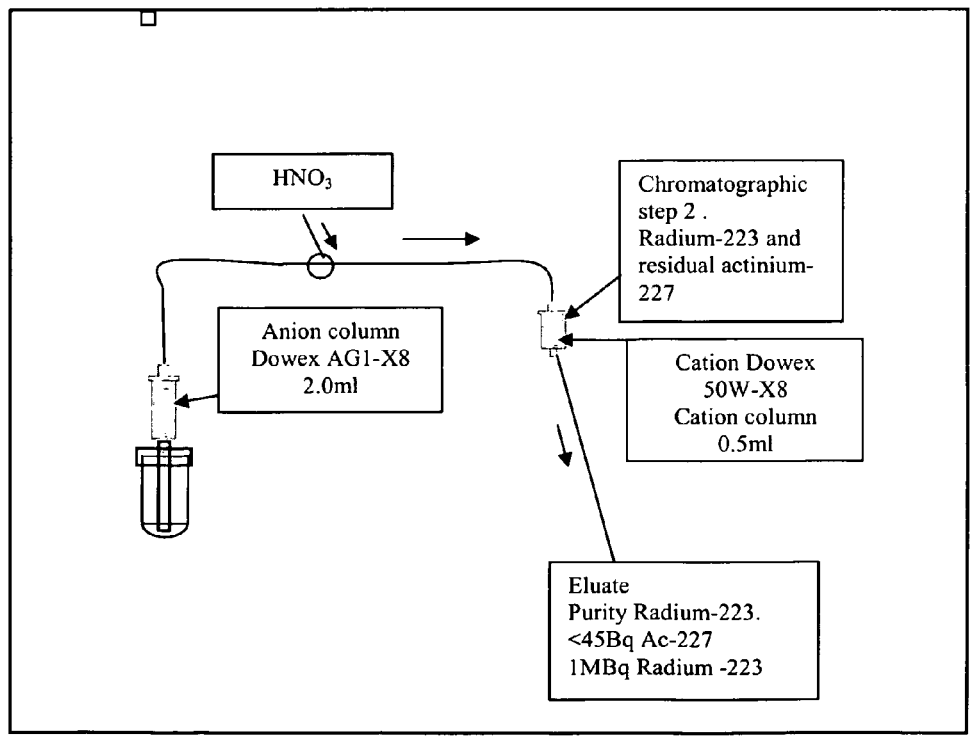
Figure 4 - setup for evaluating cation separation column.

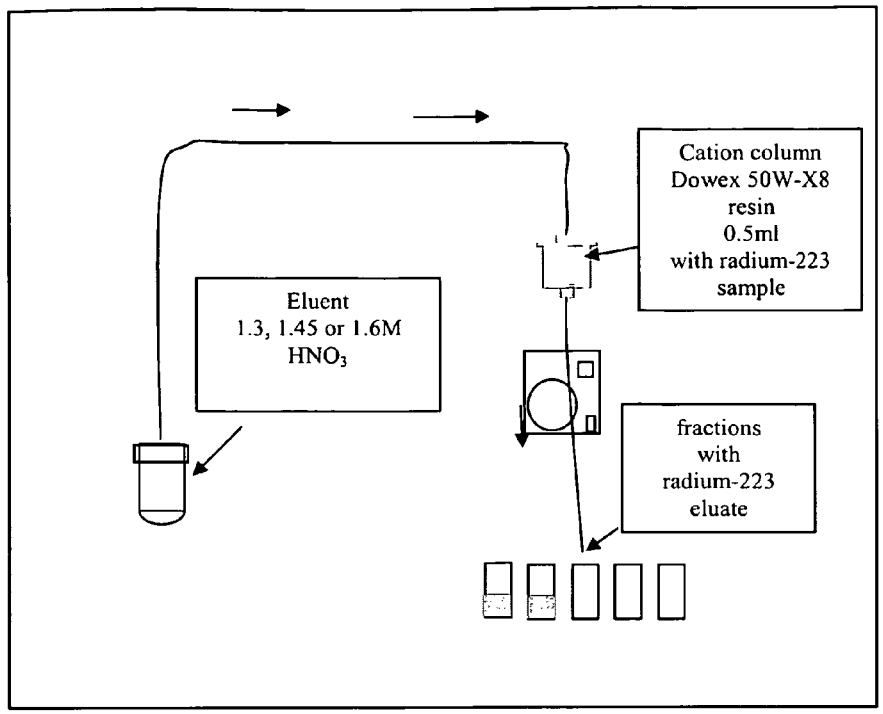
Figure 5 - set up for assessing elution of radium-223 elution from cation exchange column.
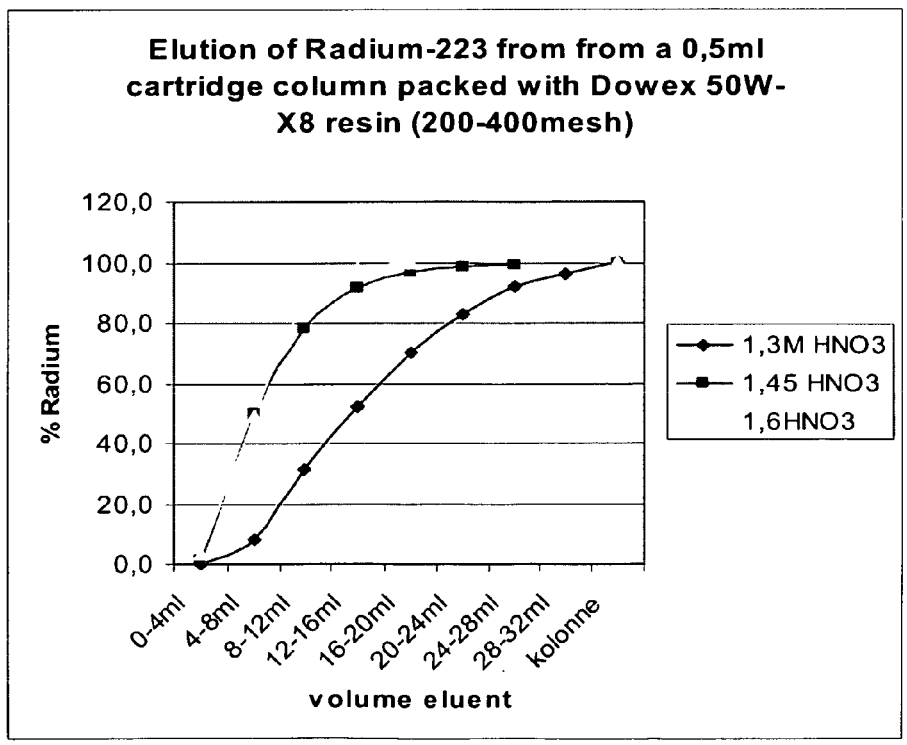
Figure 6 - elution profiles generated by the apparatus of Figure 5.

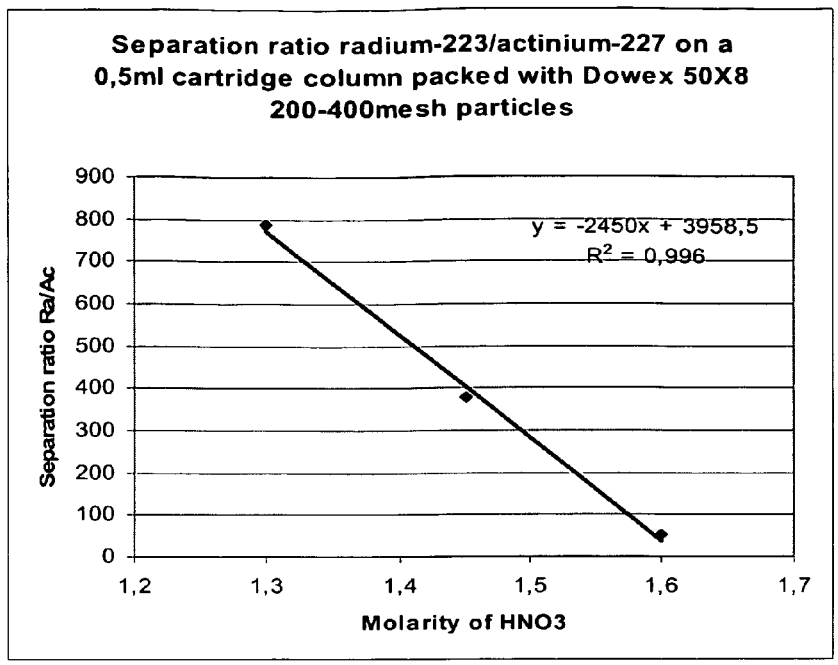
Figure 7 separation ratio between radium-223 and actinium-227 at varying HNO₃ concentrations.
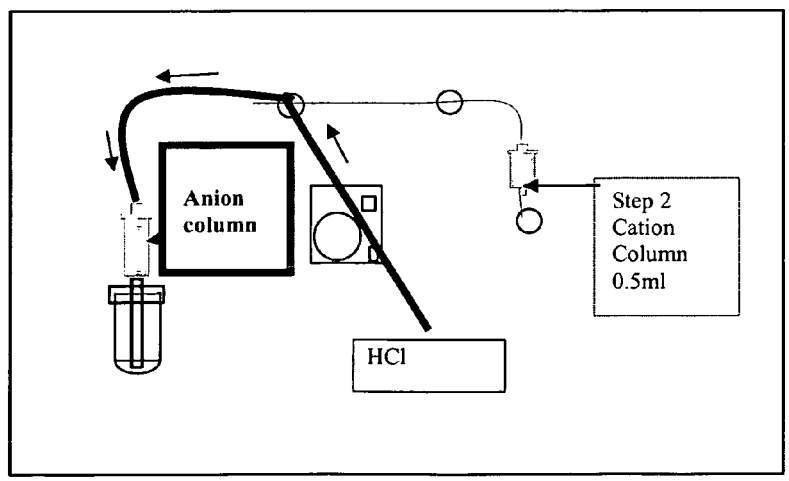
Figure 8 - regeneration of parent isotopes after radium separation.

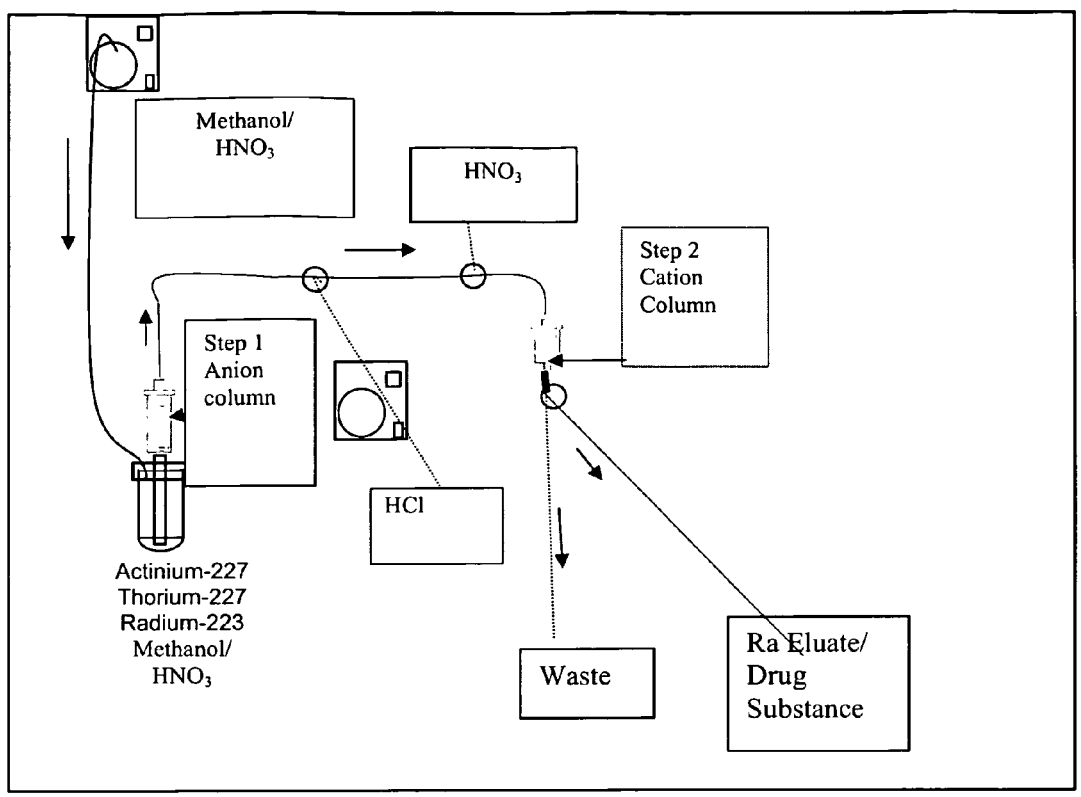
Figure 9 - Full scale experimental setup

ISOTOPE PREPARATION METHOD

CROSS-REFERENCE TO RELATED APPLICATIONS

This application is the U.S. National Stage filing under 35 U.S.C. §371 of International Application No. PCT/EP2011/002155, filed Apr. 29, 2011, which claims the benefit of priority to Great Britain Patent Application No. 1007354.2, filed on Apr. 30, 2010.

FIELD OF THE INVENTION

The present invention relates to the preparation of radium-223 ($^{223}$Ra) for pharmaceutical use. In particular, the present invention relates to methods of the commercial-scale production of radium-223 having a purity acceptable for pharmaceutical administration to human subjects.

BACKGROUND TO THE INVENTION

Specific cell killing can be essential for the successful treatment of a variety of diseases in mammalian subjects. Typical examples of this are in the treatment of malignant diseases such as sarcomas and carcinomas. However the selective elimination of certain cell types can also play a key role in the treatment of many other diseases, especially immunological, hyperplastic and/or other neoplastic diseases.

The most common methods of selective treatment are currently surgery, chemotherapy and external beam irradiation. Targeted endo-radionuclide therapy is, however, a promising and developing area with the potential to deliver highly cytotoxic radiation to unwanted cell types. The most common forms of radiopharmaceutical currently authorised for use in humans employ beta-emitting and/or gamma-emitting radionuclides. There has, however, been a recent surge in interest in the use of alpha-emitting radionuclides in therapy because of their potential for more specific cell killing. One alpha-emitting nuclide in particular, radium-223 ($^{223}$Ra) has proven remarkably effective, particularly for the treatment of diseases associated with the bone and bone-surface.

The radiation range of typical alpha emitters in physiological surroundings is generally less than 100 micrometers, the equivalent of only a few cell diameters. This makes these nuclei well suited for the treatment of tumours, including micrometastases, because little of the radiated energy will pass beyond the target cells and thus damage to surrounding healthy tissue might be minimised (see Feinendegen et al., Radiat Res 148:195-201 (1997)). In contrast, a beta particle has a range of 1 mm or more in water (see Wilbur, Antibody Immunocon Radiopharm 4: 85-96 (1991)).

The energy of alpha-particle radiation is high compared to beta particles, gamma rays and X-rays, typically being 5-8 MeV, or 5 to 10 times that of a beta particle and 20 or more times the energy of a gamma ray. Thus, this deposition of a large amount of energy over a very short distance gives α-radiation an exceptionally high linear energy transfer (LET), high relative biological efficacy (RBE) and low oxygen enhancement ratio (OER) compared to gamma and beta radiation (see Hall, "Radiobiology for the radiologist", Fifth edition, Lippincott Williams & Wilkins, Philadelphia Pa., USA, 2000). This explains the exceptional cytotoxicity of alpha emitting radionuclides and also imposes stringent demands on the level of purity required where an isotope is to be administered internally. This is especially the case where any contaminants may also be alpha-emitters, and most particularly where long half-life alpha emitters may be present, since these can potentially cause significant damage over an extended period of time.

One radioactive decay chain leading to $^{223}$Ra, which has been used as a source for this isotope in small quantities, is indicated blow. The table shows the element, molecular weight (Mw), decay mode (mode) and Half-life (in years (y) or days (d)) for $^{223}$Ra and its two precursor isotopes. This preparation begins from $^{227}$Ac, which is itself found only in traces in uranium ores, being part of the natural decay chain originating at $^{235}$U. One ton of uranium ore contains about a tenth of a gram of actinium and thus although $^{227}$Ac is found naturally, it is more commonly made by the neutron irradiation of $^{226}$Ra in a nuclear reactor.

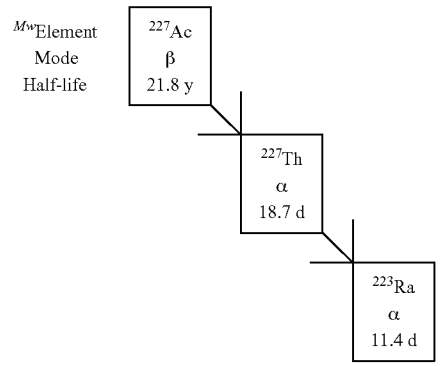

It can be seen from this illustration that $^{227}$Ac, with a half-life of over 20 years, is a very dangerous potential contaminant with regard to preparing $^{223}$Ra from the above decay chain for pharmaceutical use. In particular, although $^{227}$Ac itself is a beta-emitter, its long half-life means that even very low activities represent a significant lifetime radiation exposure, and furthermore, once it decays, the resulting daughter nuclei (i.e. $^{227}$Th) generate a further 5 alpha-decays and 2 beta-decays before reaching stable $^{207}$Pb. These are illustrated in the table below:

| | Nuclide | | | | | | | |
|---|---|---|---|---|---|---|---|---|
| | $^{227}$Th | $^{223}$Ra | $^{219}$Rn | $^{215}$Po | $^{211}$Pb | $^{211}$Bi | $^{207}$Tl | $^{207}$Pb |
| ½-life | 18.7 d | 11.4 d | 4.0 s | 1.8 ms | 36.1 m | 2.2 m | 4.8 m | stable |
| α-energy/MeV | 6.15 | 5.64 | 6.75 | 7.39 | | 6.55 | | |
| β-energy (max)/MeV | | | | | 1.37 | | 1.42 | |
| Energy % | 17.5 | 16.0 | 19.1 | 21.0 | 3.9 | 18.6 | 4.0 | |

It is evident from the above two decay tables that more than 35 MeV of energy is deposited by one $^{227}$Ac decay chain, representing a significant toxicity risk for essentially the entire lifetime of any human subject administered with $^{227}$Ac.

As a result, the content of $^{227}$Ac contaminant in $^{223}$Ra for pharmaceutical use is strictly limited to 45 Bq $^{227}$Ac in 1 MBq $^{223}$Ra. Thus for practical purposes, a method which is to provide $^{223}$Ra for pharmaceutical use should preferably provide a purity of 10 Bq $^{227}$Ac in 1 MBq $^{223}$Ra or better to ensure that this safety limit is always adhered to.

A number of studies into the purification of $^{223}$Ra have been published, primarily in environmental contexts, where the authors desire to accumulate the $^{223}$Ra from a high-volume sample so as to allow analysis of the degree of environmental contamination (e.g. Howitz et al., Reactive and Functional Polymers, 33, 25-36 (1997)).

Only one previously published method is know to have directly addressed the question of generating $^{223}$Ra with biomedical purity, and that is the method of Larsen et al. published in WO/2000/040275. This method involved permanent absorption of $^{227}$Ac and $^{227}$Th onto an f-block specific Silica Actinide Resin having P,P' di-octyl methane bisphosphonic acid binding groups on a silica support. This provided relatively high purity, of less than $4 \times 10^{-3}\%$ $^{227}$Ac in comparison with $^{223}$Ra, but required a large number of manual handling steps and was poorly suited for scaling-up or automation. Furthermore, because the resin irreversibly sorbed the mother and grandmother nuclei, the issue of radioactive damage to the resin becomes significant if such a resin is to be used for the commercial lifetime of an $^{227}$Ac source (tens of years). This is especially the case on a commercial scale, where concentrations of isotopes need to be kept as high as possible to maximise batch sizes and minimise handling volumes.

No previously known method for the generation of $^{223}$Ra addresses issues such as yield of $^{223}$Ra, speed of the purification process, automation, minimising of wasted isotopes and corresponding production or radioactive waste or any similar issues associated with commercial-scale production. Furthermore, all methods known to produce $^{223}$Ra of viable pharmaceutical purity use specialist resins which cannot be guaranteed to be available and are potentially more difficult to validate as reliable. Guseva et al. (Radiochemistry 46, 58-62 (2004)) proposed a basic generator system for $^{223}$Ra using an anion exchange method developed for extracting radium from environmental samples. This, however, was on a very small scale and never intended or indicated as providing material of pharmaceutical purity.

In view of the above, there is a considerable need for an improved method by which $^{223}$Ra may be generated and purified for pharmaceutical use at a purity appropriate for direct injection into human subjects. It would be a considerable advantage if the method were to provide a high yield of $^{223}$Ra, a low loss of $^{227}$Ac and/or $^{227}$Th parent isotopes and/or utilise widely available separation media. It would be further advantageous if the method was rapid, was viable for relatively large (commercial scale) radioactive samples, included only a minimum number of manual handling steps, and/or was suitable for automation.

BRIEF DESCRIPTION OF THE INVENTION

The present inventors have now established that by separation of a $^{227}$Ac/$^{227}$Th/$^{223}$Ra generator using a strong base anion exchange resin, followed by separation utilising a strong acid cation exchange resin, a $^{223}$Ra solution of very high radiochemical purity may be produced while providing a number of desirable advantages in the method.

In a first aspect, the present invention therefore provides a method for the generation of $^{223}$Ra of pharmaceutically tolerable purity comprising i) forming a generator mixture comprising $^{227}$Ac, $^{227}$Th and $^{223}$Ra;

ii) loading said generator mixture onto a strong base anion exchange resin;

iii) eluting said $^{223}$Ra from said strong base anion exchange resin using a first mineral acid in an alcoholic aqueous solution to give a first eluted $^{223}$Ra solution;

iv) loading the $^{223}$Ra of the first eluted $^{223}$Ra solution onto a strong acid cation exchange resin; and v) eluting the $^{223}$Ra from said strong acid cation exchange resin using a second mineral acid in aqueous solution to provide a second eluted solution.

The process will optionally and preferably also include either one or both of the steps of:

x) eluting said $^{227}$Ac and $^{227}$Th from said strong base anion exchange resin using a third mineral acid in aqueous solution, whereby to recover a mixture of $^{227}$Ac and $^{227}$Th; and y) storing said mixture of $^{227}$Ac and $^{227}$Th for a period sufficient to allow ingrowth of $^{223}$Ra by radioactive decay, whereby to re-form a generator mixture comprising $^{227}$Ac, $^{227}$Th and $^{223}$Ra.

Step x) may be carried out at any point following step iii) of the above-described process. Step y) will begin immediately following elution step iii) and may occur primarily on the anion resin (i.e. before or without step x)) and/or after recovery of the $^{227}$Ac and $^{227}$Th mixture from the resin (i.e. after step x)).

After ingrowth step y), the generator mixture may be re-used to generate a further batch of $^{223}$Ra, and a single $^{227}$Ac sample will preferably be used repeatedly (e.g. more than 10 times, such as 50 to 500 times). If the $^{227}$Ac and $^{227}$Th mixture is not eluted from the strong base anion exchange resin then the process may be repeated from step iii). Preferably, however, step x) will be carried out and the $^{227}$Ac and $^{227}$Th mixture eluted from the strong base anion exchange resin. In this case the process will be repeated from step i) or step ii).

In a further aspect, the present invention provides a solution of $^{223}$Ra comprising less than 45 Bq $^{227}$Ac per 1 MBq $^{223}$Ra, preferably a solution of $^{223}$Ra comprising less than 10 Bq $^{227}$Ac per 1 MBq $^{223}$Ra. Such a solution is optionally formed or formable by any of the methods herein described, and is preferably formed or formable by the preferred methods herein described.

BRIEF DESCRIPTION OF THE DRAWINGS

FIG. 1 shows a suitable experimental set up to determine radium-223 yield on a 2 ml anion column packed with Dowex AG1-X8 200-400 mesh particles. All radium-223 was diluted in 2 ml of eluent and loaded onto the column. The column was then washed with the same methanol/HNO$_3$ solution.

FIG. 2 shows the elution profile of radium-223 from a 2 ml anion-exchange column packed with AG 1-X8 200-400mesh particles. Three different concentrations of methanol in 0.5M HNO$_3$ are shown.

FIG. 3 shows a suitable setup for evaluation of leakage of actinium-227 from anion columns.

FIG. 4 shows a setup for evaluating a cation separation column.

FIG. 5 shows the experimental setup of radium-223 elution on a 0.5 ml column packed with Dowex 50W-X8 (200-400 mesh) particles.

FIG. 6 shows the elution profiles of radium-223 from the experimental setup shown in FIG. 5.

FIG. 7 shows concentrations of $HNO_3$ and separation ratio between radium-223 and actinium-227 (Bq) in the eluate from a 0.5 ml cation resin packed with Dowex 50W-X8 (200-400 mesh) particles.

FIG. 8 shows the flow path by which actinium-227 and thorium-227 are washed back into the generator vial.

FIG. 9 shows a full scale experimental setup for drug substance production.

DETAILED DESCRIPTION OF THE INVENTION

A very significant aspect of the present invention is the ability for the generator mixture to be stripped from the separation resin and regenerated with high efficiency. In particular, the present method relates to a process for long-term commercial use, and as such should be capable of allowing the repeated use of the generator mixture for many years. The useful life of the generator mixture will certainly be of the order of the half-life of the originating $^{227}$Ac isotope, and thus potentially several tens of years (e.g. 10 to 50 years). There are several issues which result from this which have not been addressed in any of the $^{223}$Ra production or purification systems previously described.

A first issue arising from the potentially long commercial lifetime of the generator mixture is the stability of its storage environment. Specifically, any material exposed to the generator mixture is potentially receiving more than a million beta decays per second from the $^{227}$Ac, plus around the same number of alpha decays per second from the included $^{227}$Th and up to the same number of alpha decays again from the in-growing $^{223}$Ra and from each of its alpha-emitting daughter nuclides. This is very much more concentrated than any $^{223}$Ra generator system previous proposed.

Alpha irradiation in particular is highly ionising and so over the course of a number of years, the $10^{13}$ or more alpha-decays per year to which the surroundings of the generator will be exposed is very likely to cause significant damage to any organic components in long term proximity. As a result, systems such as those described in WO/2000/040275, in which the generator is irreversibly bound to a separator resin cannot be expected to be stable even when inorganic resins are used, since the binding components closest to the radio-nuclei are organic and susceptible to damage. This will result in gradual loss of binding capacity and eventual loss of generator material and radiochemical purity of the $^{223}$Ra.

In view of the likely damage by long-term exposure, it would be a considerable advantage if the generator mixture could be recovered from the separation system so that new separation material could be used periodically. This not only avoids loss of the generator mixture but also guarantees that the purity of the product will be as high after several decades as it was when the system was first employed. The generator system will thus preferably be recovered from the separation material periodically, most preferably after every use. In the present method, this regeneration is carried out in optional and preferable step x), which occurs after elution step iii), either in parallel with the remaining steps or after they are complete.

Where a generator mixture is recovered from a separation medium it is important that this happen to a very high degree. As noted above, the actinide specific resin described for use in WO/2000/040275 does not allow for recovery of the generator mixture, since this is irreversibly sorbed. This is acceptable for laboratory or short-term testing use but is a potential problem for long-term use at a commercial scale as described above. Certain other materials, however, have been proposed for the separation of f-block elements from main-group elements, and have the potential to recover the generator mixture after use.

U.S. Pat. No. 7,553,461 describes a diglycomide (DGA) extractant which can be attached to a resin and used to separate f-block elements from those of the main group. Unlike the actinide resin previously discussed, this extractant allows for the recovery of an f-block generator mixture after separation and thus does not require that the resin be stable in perpetuity. The present inventors have, however, tested the regeneration capacity of the described DGA system and have found that under conditions optimised for efficient operation, a loss of approximately 0.1% of the $^{227}$Ac generator and around 1-5% of the $^{227}$Th intermediate isotope occurs.

The loss of only 0.1% of the generator isotope would be entirely insignificant in any laboratory or testing environment, but for a commercial system is an important factor. Assuming that the generator is used every 3rd week (after approximately 72% of the possible maximum ingrowth of $^{223}$Ra) then regeneration occurs 17 times a year, resulting in a total loss of 12% of the original $^{227}$Ac over a 10 year period. This, combined with the natural decay loss due to the 21 year half-life of the isotope increases the total reduction in activity from 73% due to natural decay down to 61% including the regeneration loss. At 21.8 years, this effect is still more dramatic, taking the 50% activity expected after one half-life down to approximately 35% and evidently reducing the useful commercial life of the system by this stage.

In the present method, the regeneration of the generator mixture has been shown to lose around 0.01% of the original $^{227}$Ac at each regeneration cycle. This loss is ten times less than the inventors can achieve with an optimised system employing a diglycomide (DGA) extractant. This applies even up to commercial scales, such as for a 2.5 GBq batch. Taking again a 3-week cycle, this would result in only around 1.2% loss of $^{227}$Ac over 10 years with this method compared to the loss of 12% with diglycomide (DGA) extractant column even under optimised conditions. Evidently this could provide many additional years of useful commercial life in comparison with the DGA resin system.

Furthermore, the present inventors have established that around 99.8% of the $^{227}$Th in the generator can be regenerated by elution from the basic anion resin as described herein. This is also significantly better than can be achieved under optimised conditions using a diglycomide (DGA) extractant, which gave a maximum of 95-99% regeneration of $^{227}$Th. This has is not only significant for the rate of ingrowth of radium, but both the column lifetime is extended and the resulting waste will contain less radioactivity and thus pose less of a disposal hazard.

In the present invention, optional but highly preferred step x) comprises eluting said $^{227}$Ac and $^{227}$Th from said strong base anion exchange resin using a third mineral acid in aqueous solution, whereby to provide a mixture of $^{227}$Ac and $^{227}$Th. This step and the entities referred to therein may have the following preferable features, either individually or in any viable combination, and optionally in any viable combination with any of the features of the other steps as described herein:

a) The optional step x) may occur after every occasion that the $^{227}$Ac is eluted from the basic anion exchange resin (i.e. after every step iii)), after every two occasions, or after every three, four or five occasions. Preferably step x) occurs between every elution step iii) and the next occasion an elution step iii) is made.

b) The third mineral acid may be an acid selected from $H_2SO_4$, $HClO_4$ and HCl, preferably HCl;

c) The third mineral acid should preferably be used at an amount so all nitrate coupled to the anion resin are washed out from the resin, and the ionic groups on the resin is replaced with another ion. Preferable this mineral acid is used with excess compared to the amount of ionic groups on the anion resin. A strength and volume of the third mineral acid will be around 3M and 10 ml when a column with size of 2 ml and with 1.2 mmol/ionic groups pr ml is stripped for $^{227}$Ac and $^{227}$Th, If $HNO_3$ are used for regeneration the regeneration of $^{227}$Th will not be effective but $^{227}$Ac will be removed.

d) In one optional embodiment, the third mineral acid in aqueous solution does not comprise any significant amount (e.g. less than 0.1% v/v) of any alcohol selected from methanol, ethanol and isopropanol. The aqueous solution may be substantially free of methanol;

e) The elution of said $^{227}$Ac and $^{227}$Th from said strong base anion exchange resin may regenerate greater than 99.9% (e.g. 99.9 to 100%) of the $^{227}$Ac loaded onto the resin in step ii). Preferably this will be greater than 99.95, Around 99.99% is most preferred.

f) The elution of said $^{227}$Ac and $^{227}$Th from said strong base anion exchange resin may regenerate greater than 85% (e.g. 85 to 99.95%) of the $^{227}$Th loaded onto the resin in step ii). Preferably this will be greater than 95%, and more preferably at least 98%. Around 99.8% is most preferred.

It is further of significance that the DGA resin described above is only demonstrated to provide a separation efficiency of $10^2$ for $^{223}$Ra over $^{227}$Ac (U.S. Pat. No. 7,553,461, column 19 line 9). Not only is it highly surprising that a simple basic anion exchange resin when used under the conditions indicated herein can provide at least $10^4$ separation in comparison, but furthermore this degree of separation is essential in order to provide an isotope with sufficient radiochemical purity to meet pharmaceutical standards.

With regard to optional but highly preferable step y), the regeneration of the $^{223}$Ra will begin by natural radioactive decay as soon as the existing $^{223}$Ra is eluted in step iii). It is preferable to allow sufficient time for significant ingrowth of $^{223}$Ra before the generator mixture is again separated, and the period which is suitable will depend upon the nature of the mixture, as discussed above. Preferably, the regeneration of the mixture will be sufficiently effective (as described herein) that the level of $^{227}$Ac activity and $^{227}$Th activity will be close to equal, (e.g. within 5%) and in such circumstances a period of around 14 to 50 days is suitable for allowing ingrowth of $^{223}$Ra. This would provide between around 460 MBq and 950 MBq $^{223}$Ra from a theoretical mixture of 1 GBq $^{227}$Ac and 1 GBq $^{227}$Th. Where the $^{227}$Th level is significantly depleted by reduced regeneration, this period will be longer, particularly towards the shorter end of the range. The skilled worker will have no difficulty selecting a suitable ingrowth period based upon the characteristics of each particular system.

The present invention provides a method for the production of $^{223}$Ra at a purity suitable for use in endo-radionuclide therapy. A number of preferred features of the system are indicated below, each of which may be used in combination with any other feature where technically viable, unless indicated otherwise.

The methods and all corresponding embodiments of the invention will preferably be carried out on a commercial scale and thus will be capable and suitable for use at this scale while maintaining all of the other characteristics described herein as appropriate (such as radionuclear purity, optionally methanol content etc). A commercial scale will typically be a scale greater than that required for the treatment of a single subject, and may be, for example, the purification of more than 10, preferably more than 25 and most preferably more than 45 typical doses of $^{223}$Ra. Evidently, a typical dose will depend upon the application, but anticipated typical dose may be from 0.5 to 100 MBq, preferably 1 to 50 MBq, most preferably around 2 to 25 MBq.

Step i) of the method of the invention relates to preparing a generator mixture comprising $^{227}$Ac, $^{227}$Th and $^{223}$Ra. Such a mixture will inherently form by the gradual decay of a sample of $^{227}$Ac, but for use in the invention will preferably also have one or more of the following features, either individually or in any viable combination:

a) a $^{227}$Ac radioactivity of at least 500 MBq (e.g. 500 MBq to 50 GBq), preferably at least 1 GBq, more preferably at least 2.5 GBq;

b) a $^{223}$Ra radioactivity of at least 100 MBq (e.g. 100 MBq to 50 GBq), preferably at least 350 MBq, more preferably at least 1 GBq;

c) a volume of no more than 50 ml (e.g. 0.1 to 50 ml), preferably no more than 10 ml, more preferably no more than 5 ml.

Step ii) of the method of the invention relates to the loading of the generator mixture onto a strong base anion exchange resin. This step and the entities referred to therein may have the following preferable features, either individually or in any viable combination, and optionally in any viable combination with any of the features of the other steps as described herein:

a) The strong base anion exchange resin may be a polystyrene/divinyl benzene copolymer based resin, preferably containing 1-95%; divinyl benzene b) The strong base anion exchange resin may be an R—N$^+$Me$_3$ type (type I) resin or an R—N$^+$Me$_2$CH$_2$CH$_2$OH (Type II) resin, preferably a type I resin;

c) The strong base anion exchange resin may have an exchange capacity of 0.2 to 5 meq/ml, preferably 0.6 to 3 meq/ml, most preferably 1 to 1.5 meq/ml (e.g. around 1.2 meq/ml);

d) The strong base anion exchange resin may have a particle size grading of 10 to 800 mesh, preferably 50 to 600 mesh, more preferably 100 to 500 mesh (e.g. around 200 to 400 mesh).

e) The strong base anion exchange resin may be used in the form of a column.

f) The volume of resin used (e.g. when packed in a column) may be 10 ml or less, (e.g. 0.5 to 10 ml), preferably 5 ml or less, more preferably 1 to 2.5 ml (e.g. around 2 ml).

g) The strong base anion exchange resin may be DOWEX 1X8 (e.g. DOWEX AG 1X8) or equivalent resin with a 200-400 mesh size.

Step iii) of the method of the invention relates to eluting the $^{223}$Ra from said strong base anion exchange resin using a first mineral acid in an alcoholic aqueous solution to give a first eluted $^{223}$Ra solution. This step and the entities referred to therein may have the following preferable features, either individually or in any viable combination, and optionally in any viable combination with any of the features of the other steps as described herein:

a) The first mineral acid may be an acid selected from $H_2SO_4$ or $HNO_3$ preferably $HNO_3$.

b) The first mineral acid may be used at a concentration of 0.1 to 5 M, such as 0.1 to 3 M or 0.1 to 1.5 M, preferably 0.3 to 0.8 M, more preferably 0.45 to 0.55M (e.g. around 0.5M), particularly where the first mineral acid is $HNO_3$; or alternatively, b') The first mineral acid may be used at a concentration of 0.1 to 5 M, such as 0.1 to 3 M or 0.1 to 1.5 M, preferably 1 to 1.5 M, more preferably 1.25 to 1.35M (e.g. around 1.3M), particularly where the first mineral acid is $HNO_3$;

c) The alcoholic aqueous solution may comprise at least one alcohol selected from methanol, ethanol and isopropanol, preferably methanol;
d) The alcoholic aqueous solution may comprise 20 to 95% methanol, e.g. 75 to 90% methanol, more preferably 83 to 87% methanol (e.g. around 85% methanol); or alternatively,
d') The alcoholic aqueous solution may comprise 20 to 95% methanol, e.g. 75 to 90% methanol, more preferably 79 to 84% methanol (e.g. around 81% methanol);
e) The alcoholic aqueous solution may comprise around 0.5 M $HNO_3$ in around 85% aqueous methanol; or alternatively,
e') The alcoholic aqueous solution may comprise around 1.3 M $HNO_3$ in around 81% aqueous methanol
f) The $^{223}$Ra may be eluted from said strong base anion exchange resin using 10 to 100 column volumes of the first mineral acid in an alcoholic aqueous solution. Preferably the amount will be 15 to 50 column volumes, more preferably 20 to 40 column volumes (e.g. around 30 column volumes).
g) The first eluted solution will preferably have a contamination level of no more than 100 (e.g. 1 to 100) Bq $^{227}$Ac per 1 MBq $^{223}$Ra, more preferably no more than 45 Bq $^{227}$Ac per 1 MBq $^{223}$Ra (e.g. no more than 30) and most preferably no more than 10 Bq $^{227}$Ac per 1 MBq $^{223}$Ra;
h) The steps of loading the generator mixture onto the base anion exchange resin and eluting the first eluted $^{223}$Ra solution may provide a separation ratio of $^{223}$Ra to $^{227}$Ac of at least 10,000:1 (e.g. 10,000:1 to 500,000:1), preferably at least 20,000:1, more preferably at least 30,000:1.
i) The $^{223}$Ra may be eluted from said strong base anion exchange resin in uncomplexed form, such as in the form of a sample salt in solution (e.g. as the salt of the first mineral acid).
j) Optionally, the use of complexing agents such as DTPA may be avoided, and in one embodiment all solutions used in step ii and/or step iii are substantially free of complexing agents, such as DTPA.

Step iv) of the method of the invention relates to loading the $^{223}$Ra eluted from the anion exchange resin onto a strong acid cation exchange resin. This step and the entities referred to therein may have the following preferable features, either individually or in any viable combination, and optionally in any viable combination with any of the features of the other steps as described herein:
a) The strong acid cation exchange resin may be a polystyrene/divinyl benzene copolymer based resin, preferably containing 1-95% DVB;
b) The strong acid cation exchange resin may be an $SO_3H$ type.
c) The strong acid cation exchange resin may have an exchange capacity of 0.2 to 5 meq/ml, preferably 0.6 to 3 meq/ml, most preferably 1 to 2 meq/ml (e.g. around 1.7 meq/ml);
d) The strong acid cation exchange resin may have a particle size grading of 10 to 800 mesh, preferably 50 to 600 mesh, more preferably 100 to 500 mesh (e.g. around 200 to 400 mesh).
e) The strong acid cation exchange resin may be used in the form of a column.
f) The volume of resin used (e.g. when packed in a column) may be 5 ml or less, (e.g. 0.1 to 5 ml), preferably 2 ml or less, more preferably 0.2 to 1 ml (e.g. around 0.5 ml).
g) The strong acid cation exchange resin may be DOWEX 50WX8 or equivalent resin with a 200-400 mesh size.

Step v) of the method of the invention relates to eluting the $^{223}$Ra from said strong acid cation exchange resin using a second mineral acid in aqueous solution to provide a second eluted solution. This step and the entities referred to therein may have the following preferable features, either individually or in any viable combination, and optionally in any viable combination with any of the features of the other steps as described herein:
a) The second mineral acid may be an acid selected from $H_2SO_4$, $HNO_3$ and HCl, preferably $HNO_3$;
b) The second mineral acid may be used at a concentration of 0.5 to 5 M, preferably 1 to 2 M, more preferably 1.0 to 1.6M (e.g. around 1.3 M), particularly where the second mineral acid is $HNO_3$;
c) The aqueous solution preferably does not comprise any significant amount (e.g. less than 0.1% v/v) of any alcohol selected from methanol, ethanol and isopropanol. Preferably the aqueous solution is substantially free of methanol;
d) The $^{223}$Ra may be eluted from said strong acid cation exchange resin using 10 to 100 column volumes of the second mineral acid in aqueous solution. Preferably the amount will be 15 to 80 column volumes, more preferably 30 to 60 column volumes.
g) The second eluted solution will preferably have a contamination level of no more than 1 (e.g. 0.0001 to 1) Bq $^{227}$Ac per 1 MBq $^{223}$Ra, more preferably no more than 0.1 Bq $^{227}$Ac per 1 MBq $^{223}$Ra and most preferably no more than 0.05 Bq $^{227}$Ac per 1 MBq $^{223}$Ra;
h) The second eluted solution will preferably have a methanol content of not more than 30 mg per dose of $^{223}$Ra, preferably no more than 10 mg, and more preferably no more than 2 mg per dose.
i) The steps of loading the first eluted solution onto the acid cation exchange resin and eluting the second eluted $^{223}$Ra solution may provide a separation ratio of $^{223}$Ra to $^{227}$Ac of at least 10:1 (e.g. 10:1 to 10,000:1), preferably at least 100:1, more preferably at least 500:1.
j) The $^{223}$Ra may be eluted from said strong acid cation exchange resin in uncomplexed form, such as in the form of a sample salt in solution (e.g. as the salt of the first mineral acid).
k) The use of complexing agents such as DTPA may be avoided, and in one embodiment all solutions used in step iv and/or step v are substantially free of complexing agents.

In addition to the above steps, the methods of the invention and all corresponding aspects may comprise additional steps, for example to validate the purity of the $^{223}$Ra for pharmaceutical purposes, to exchange counter-ions, concentrate or dilute the solution or to control factors such as pH and ionic strengths. Each of these steps thus forms an optional but preferable additional step in the various aspects of the present invention.

In the Examples below, it is determined that by suitable optimisation of the process, one can achieve purification of $^{223}$Ra to a pharmaceutical level of radiochemical purity (see above, all of which disclosures apply where context allows) using only a single strong base anion exchange separation step. Therefore, in an alternative aspect, the present invention provides for a method for the generation of $^{223}$Ra of pharmaceutically tolerable purity comprising
i) preparing a generator mixture comprising $^{227}$Ac, $^{227}$Th and $^{223}$Ra;
ii) loading said generator mixture onto a strong base anion exchange resin;
iii) eluting said $^{223}$Ra from said strong base anion exchange resin using a first mineral acid in an alcoholic aqueous solution to give a first eluted $^{223}$Ra solution;

Evidently, all of steps i) to iii) will preferably be carried out as described herein, and all of the appropriate preferred aspects and embodiments described herein will apply to the invention implemented in this alternative way. The remaining steps described herein may optionally be used in addition to these three core steps and alternatively or additionally, the additional validation and other manipulation steps described above may also be used in any combination.

The invention will now be illustrated further by reference to the following non-limiting examples and the attached figures, in which:

FIG. 1 Illustrates a continuous chromatographic process to produce pure Radium-223 from an Actinium-227 source as described herein. Pharmaceutical purity $^{223}$Ra is eluted from the cation exchange column.

FIG. 2 Illustrates the apparatus of FIG. 1 with additional trapping and clean-up steps to verify the purity of the $^{223}$Ra and to control the counter-ions and other properties of the solution.

EXAMPLES

Overview

A process for separation of $^{223}$Ra from a $^{227}$Ac/$^{227}$Th generator system was set up as indicated in FIG. 1. Specifically, a $^{227}$Ac/$^{227}$Th storage vessel is arranged such that the contents may be loaded onto a strong base anion exchange resin. The elution solvent is initially chosen so as to elute the $^{223}$Ra selectively while retaining the $^{227}$Th and $^{227}$Ac on the anion column. These isotopes are later eluted with a further solvent and returned to the generator storage vessel. The eluted $^{223}$Ra from the strong base anion column is then evaporated and/or re-suspended as necessary before loading onto a strong acid cation exchange column. Again, the $^{223}$Ra is selectively eluted using a second elution solvent to give $^{223}$Ra at a radioisotopic purity suitable for pharmaceutical use. The purified $^{223}$Ra is then optionally subjected to various clean-up and validation steps to ensure that the final solution is suitable and ready for pharmaceutical use.

Each of the key steps in the above embodiment was optimised by the present inventors so as to provide a very high purity product obtainable on a commercial scale in a process having the minimum of manual handling steps. Only once optimised is it evident that a product of pharmaceutical purity and above can be obtained with such a small number of simple, largely automated steps.

Example 1

Anion Exchange Column 1.1 Radium-223 Yield on Anion Column.

During development of a radium-223 purification procedure, the yield of radium-223 in the process is an important issue. To be able to determine the amount of solution one must use to obtain high yield of radium-223, pure radium-223 was loaded onto 2.0 ml cartridge column packed with Dowex 1-X8 200-400 mesh anion particles.

The radium-223 was eluted from three different columns with 80, 82.5 and 85% methanol respectively. The concentration of HNO$_3$ was 0.5M in all three experiments. The volume needed to obtain around 95% yield of radium-223 in this chromatographic step was determined.

FIG. 1 shows a suitable experimental set up to determine radium-223 yield on a 2 ml anion column packed with Dowex AG1-X8 200-400 mesh particles. All radium-223 was diluted in 2 ml of eluent and loaded onto column. The column was then washed with the same methanol/HNO$_3$ solution.

FIG. 2 shows the elution profile of radium-223 from a 2 ml anion-exchange column packed with AG 1-X8 200-400 mesh particles. Three different concentrations of methanol in 0.5M HNO$_3$ are shown.

Note the washed columns are also included in the figure to obtain total accounts of radium-223.

Comments

Radium-223 elutes slower from the anion resin when the concentration of methanol increases.

1.2 Actinium-227 Leakage from Anion Column.

To retain most of the actinium-227 on the anion exchange resin, initial experiments showed that the level of methanol must be 80% or above. This is correct when nitric acid concentration is fixed to 0.5M. If nitric acid concentration is increased, the concentration of methanol might be decreased and the same result can be achieved.

Around 25% of actinium-227 leaked into the radium-223 eluate from the anion column when 10 ml of 70% methanol in combination with 0.5M HNO$_3$ was used. (See Table 1). If the methanol concentration was increased to 80%, less than 0.2% actinium-227 leaked through the anion column when the same amount of eluent (10 ml) was used. (See Table 1)

TABLE 1

Actinium-227 level in radium-223 eluate from a 2 ml cartridge column packed with Dowex 1-X8 200-400 mesh particles.

| Eluent | Actinium-227 level in eluate in % of total load of actinium-227 |
|---|---|
| 10 ml 70% Methanol/0.5M HNO$_3$ | 23.8 |
| 10 ml 75% Methanol/0.5M HNO$_3$ | 1.3 |
| 10 ml 80% Methanol/0.5M HNO$_3$ | <0.2 |

From these results it was clear that the leakage of actinium-227 from the resin was dependent of the level of methanol. It was also clear that a quite small difference in the concentration of methanol gave a high impact regarding the leakage of Actinium-227.

As one can see from the above table, the level of methanol, when used in combination with 0.5M HNO$_3$, must be 80% or greater if almost all actinium-227 is to be retained. Based on this knowledge, an experiment was set up to study 80-85% methanol in combination with 0.5M HNO$_3$.

FIG. 3 shows a suitable setup for evaluation of leakage of actinium-227 from anion columns. All columns where packed with Dowex AG1-X8 200-400 mesh particles. The running conditions was 0.5M HNO$_3$ with 80, 82.5 and 85% methanol respectively. In all runs a generator with 180 MBq Actinium was used. All actinium-227 samples where diluted in 2 ml of eluent and loaded onto column. The column was then washed with the same methanol/HNO$_3$ solution.

TABLE 2

Amount of actinium-227 measured in eluate (Cation column) after 180 MBq of actinium-227 source was loaded onto a 2 ml cartridge column packed with Dowex AG1-X8 200-400 mesh particles.

| Eluent | *Volume of Eluent | Leakage of actinium-227 eluate in Bq or % of total load of actinium-227 | **Separation ratio actinium-227 trapped on column/actinium-227 in eluate |
|---|---|---|---|
| 80% Methanol 0.5M HNO$_3$ | 35 | 5800 Bq/(0.0032%) | 3.1 * 10$^4$ |

TABLE 2-continued

Amount of actinium-227 measured in eluate (Cation column) after 180 MBq of actinium-227 source was loaded onto a 2 ml cartridge column packed with Dowex AG1-X8 200-400 mesh particles.

| Eluent | *Volume of Eluent | Leakage of actinium-227 eluate in Bq or % of total load of actinium-227 | **Separation ratio actinium-227 trapped on column/actinium-227 in eluate |
|---|---|---|---|
| 82.5% Methanol 0.5M $HNO_3$ | 50 | 280 Bq/(0.00016%) | $6.4 * 10^5$ |
| 85% Methanol 0.5M $HNO_3$ | 60 | 385 Bq/(0.00021%) | $4.7 * 10^5$ |

*To obtain 95% yield of radium-223 in the process the volume of eluent used in this experiment varies.
**Measurements are performed between 40-50 days after separation.

Discussion

The result shows that a combination of higher volume and higher methanol concentration reduces the leakage of actinium-227. The volumes used in this experiment have been based on the volumes that give around 95% yield of radium-223.

One can observe that most actinium-227 was retained on the column. To fulfil specification regarding actinium-227 level in drug substance, the separation ratio between "retained" actinium-227 and "leaked" actinium 227 must be around $3.0*10^4$. For all experiments this criteria is fulfilled. At 85% methanol the criteria is fulfilled by a factor of 15.

The leakage of actinium-227 from the anion column is so low that it will have no impact of the recovery of actinium-227 in the process. This separation step is the first and most important step in the whole chromatographic process. It shows that is important to have stringent control of the concentration of methanol when the eluent is prepared. This is crucial to obtain low leakage of actinium-227 from the column and thus the methanol concentration should be carefully correlated to the desired $HNO_3$ concentration.

It is probably possible to use higher concentrations of methanol to obtain even better separation. However the volumes will be larger and the separation time and waste volume will increase.

Example 2

Cation Exchange Column

The main purpose of this chromatographic step is:
Trap radium-223 from chromatographic step 1.
Remove most of the methanol used in the first separation step.
Further purification/polishing of radium-223 from actinium-227.

2.1 Trapping of Radium-223

It has been shown in the development of the present process that suitable cation exchange columns can binds radium-223 when the molarity of acid is in the range 1M or lower. Dowex 50W-X8 cation exchange media shows in addition increased affinity for radium-223 when methanol is present in the eluent.

During the development of this process it has been verified that the affinity for radium-223 to a suitable cation exchange resin is high. When 60 ml radium-223 eluate is pumped through a 0.5 ml cation column with 85% methanol/0.5M $HNO_3$ all radium-223 is trapped.

2.2 Removal of Methanol

Methanol is a class 2 solvent, it is preferable to keep the amount of methanol in drug product as low as possible. The PDE (personal daily exposure) for this solvent should not exceed 30 mg/day. The level of methanol in the drug liquid should also be less than 3000 ppm (European Medicines Agency (EMEA)).

Approximately 99.75% of the methanol used in this process is removed by simply passing the eluent through the column to waste. This is the major removal step of methanol in the process. Since the cation resin is low (e.g. only 0.5 ml) in volume, the amount of methanol remaining on this column after this chromatographic step will be low.

A rough estimate is that a 0.5 ml column packed with Dowex 50W-X8 cation exchange resin 200-400 mesh will contain around 0.15 ml liquid or around 100 mg of methanol when the column is pumped dry. If this entire methanol was transferred to drug product more than 4 doses must be prepared from this eluate to fulfil the PDE of 30 mg/day. The eluate must also be diluted so the level of methanol is lover than the 3000 ppm set by the EMEA ref 5.

2.3 Yield of Radium-223

To be able to have an effective process for purifying radium-223 it is important that the loss of radium-223 in different steps in the process is as low as possible. An experiment was set up to verify the amount of eluent necessary to achieve 95% yield of radium-223 from the 0.5 ml cation exchange column. The cation column was packed with Dowex 50W-X8 200-400 mesh particles. The concentrations of $HNO_3$ evaluated where 1.3, 1.45 and 1.6M.

FIG. 5 shows the experimental set up of radium-223 elution on a 0.5 ml column packed with Dowex 50W-X8 200-400 mesh particles. The eluents tested where 1.3M, 1.45M and 1.6M $HNO_3$ FIG. 6 shows the elution profiles of radium-223 from experiment setup shown in FIG. 5.

Comments

The affinity for radium-223 on the resin was found to increase at lower concentration of $HNO_3$. The volume needed for elution of for example 95% of radium-223 on a column will increase with decreasing concentration of $HNO_3$.

Table 3 shows cumulative yield of radium-223 from a small cation column packed with Dowex 50W-X8 (200-400 mesh) particles in different concentrations of $HNO_3$. This is corresponds to the data shown in FIG. 6.

| Volume | Yield of radium-223 in % (cumulative) 1.3M $HNO_3$ | Yield of radium-223 in % (cumulative) 1.45 $HNO_3$ | Yield of radium-223 in % (cumulative) 1.6 $HNO_3$ |
|---|---|---|---|
| 0-4 ml | 0.3 | 1.3 | 3.7 |
| 4-8 ml | 8.3 | 49.9 | 49.2 |
| 8-12 ml | 31.3 | 78.5 | 87.2 |
| 12-16 ml | 52.3 | 91.6 | 98.0 |
| 16-20 ml | 70.1 | 96.7 | 99.7 |
| 20-24 ml | 82.8 | 98.7 | |
| 24-28 ml | 92.4 | 99.2 | |
| 28-32 ml | 96.4 | | |
| Column | 100 | 100.0 | 100.0 |

Comments.

From these results, elution profiles for radium-223 from a 0.5 ml column packed with Dowex 50W-X8 resin (200-400 mesh) in 1.3M, 1.45M and 1.6M $HNO_3$ are given. There is a noticeable difference between lowest and the two highest concentration of $HNO_3$ evaluated. To acquire around 95%, yield of radium-223, the following volumes and concentrations of $HNO_3$ have to be used:
1. 30M $HNO_3$: 32 ml
1. 45M $HNO_3$: 20 ml
1. 60M $HNO_3$: 16 ml To be able to select the concentration of $HNO_3$ one shall use in the process, the separation ratio between radium-223 and actinium-227 must be investigated for the above tested concentration of $HNO_3$. This experiment is shown below.

2.4 Separation Ratio Radium-223/Actinium-227

The previous Examples revealed the volume and concentration of $HNO_3$ one must use to elute 95% of radium-223 from a 0.5 ml column packed with Dowex 50W-X8 (200-400 mesh) particles. There is also of great interest to verify the separation ratio between actinium-227 and radium-223 under the same conditions.

The setup in this experiment is similar to the setup given in FIG. 5 but with actinium-227 as sample.

A 0.5 MBq actinium-227 sample in equilibrium with it's daughters where loaded onto 0.5 ml column.

The volumes and concentrations of $HNO_3$ in this experiment is identical to the one that gave 95% yield of radium-223 in previous Example.

The separation ratio obtained for radium-223 and actinium-227 is given in FIG. 7 and Table 4. The measurement of actinium-227 is based on ingrowth of actinium-227's daughter Thorium-227.

FIG. 7—shows concentrations of $HNO_3$ and separation ratio between radium-223 and actinium-227 (Bq) in the eluate from a 0.5 ml cation resin packed with Dowex 50W-X8 (200-400 mesh) particles.

Comment.

There is established to be a linear relationship between separation ratio between radium-223 and actinium-227 and the molarity of $HNO_3$ used.

Table 4 Shows concentrations and volumes as well as separation ratio between radium-223 and actinium-227 (Bq) in the eluate from a 0.5 ml cartridge column packed with Dowex 50W-X8 (200-400 mesh) cation particles.

| Concentration of $HNO_3$ (M) | *Volumes of Eluent used (ml) | Radium-223 Bq/Actinium-227 Bq in eluate |
|---|---|---|
| 1.3 | 32 | 787 |
| 1.45 | 20 | 379 |
| 1.6 | 16 | 52 |

*Volumes used gave 95% yield of radium-223 from the 0.5 ml cation resin.

Conclusion.

The separation of radium-223 and actinium-227 on a cation resin increases when molarity of $HNO_3$ decreases. The best separation between radium-223 and actinium-227 in this case was with 1.3M $HNO_3$. According to this result the selected conditions for this chromatographic step are 1.3M $HNO_3$ and 30-35 ml of eluent. The yield of radium-223 is then around 95%. The separation ratio in Bq between radium-223 and actinium-227 is close to 800.

It is probably possible to use lower concentrations of acid to obtain even better separation. Then the volumes will increase and the separation time and waste volume will also increase.

2.6 Purity of Radium Eluate:

If one use 85% methanol/0.5M $HNO_3$ in the anion exchange chromatographic step then the separation ratio between radium-223 and retained actinium-227 is approximately $4.7*10^5$. In the cation exchange chromatographic step the separation ration between Radium-223 and Actinium-227 is around 750 under appropriate conditions.

The overall separation ratio (Bq) between these two nuclides will be in the range of:

$$4.7*10^5*750=3.5*10^8$$

3 Regeneration of Actinium-227 and Thorium-227

The main purpose of this step is to regenerate actinium-227 and thorium-227 from the separation medium for future use in repetitions of the process.

Washing of actinium-227 and thorium-227 from the anion resin back into the generator vial is an important issue. The loss of actinium-227 will have direct impact on production quantities of radium-223 over time. Reducing the loss of thorium-227 is also important, since a loss here will give slower ingrowth of radium-223 from the generator.

FIG. 8 shows the flow path by which actinium-227 and thorium-227 is washed back into the generator vial.

Comments

Thorium-227 and actinium-227 is most probably present as nitrate complex on the anion exchange column. This complex must be removed so thorium-227 and actinium-227 can be recycled.

By using 10 ml 3M HCl, Cl$^-$ replaces nitrate as counter ion on the resin. When this is take place the actinium/thorium nitrate complex will not more be present on the resin. Then actinium-227 and thorium-227 do not have affinity for the resin and will elute. There are several other factors that will assist in securing an effective stripping of actinium-227 and thorium-227:

1. The density of 3M HCl is higher than the density of the methanol solution present in the particle when the stripping procedure starts. This density difference will contribute to a more effective washing procedure of the particles.
2. Thorium-227 and actinium-227 have also the same charge as the ionic groups on the resin; this is also advantageous for effective recycling of the nuclides.
3. The size of the particles employed in this case is relatively small. Small particles size is preferable obtain an effective washing procedure.
4. It is also important that the flow rate is lower than (the 1-2 ml/min in this case) used in the separation process, so the contact time in the stripping procedure is increased. A flow rate less than half of the separation rate (e.g. 0.5 ml/min or less) is recommended.

Evaporation of 10 ml of 3M HCl must be carried out prior to next separation/harvesting of radium-223 from the generator.

Example 3

Technical Production of Drug Substance from a 2.5 GBq Actinium-227 Source

After the initial experiments a full scale experiment was set up. The generator was around 2.5 GBq actinium-227. The amount of Radium-223 in the batch at the separation time was estimated to be 1.2 Gbq.

FIG. 9 shows a full scale experimental setup for drug substance production.

Comments.

The separation was performed and the result confirmed the expectations. The process produced the drug substance in a quantity of approximately 1100 MBq Radium-223. This corresponds to an overall yield in the process of 92% since the total amount of radium-223 in the generator at separation time was estimated to be 1.2 GBq. The purity was determined to be well within the requirements for pharmaceutical administration and the recovery of the parent isotopes was high, as detailed below.

Measurements with HPGe Detector.

Table 6 gives level of thorium-227, radium-223 and actinium-227 in the different fractions/column from the batch. The measurements have been performed at different times after separation. The level given for actinium-227 is likely to be an overestimation since full decay of thorium-227 has not occurred.

Table 6 shows level of actinium-227, thorium-227 and radium-223 in different fractions from columns in the technical production batch.

|  | Radium-223 level at separation day Calculated Bq* | Thorium-227 level at separation day Calculated Bq** | Actinium-227 level at separation day Calculated Bq*** |
|---|---|---|---|
| Anion column | <2360 | 1.86 * 10$^6$ | 2.96 * 10$^5$**** |
| Small cation column 0.5 ml | 1.9 * 10$^7$ | 9928 | 619 |
| Radium eluate | 1.1 * 10$^9$ | Not measured | Not measured |

*Radium level is calculated on measurement 13 days after separation
**Thorium-227 is calculated based on that all thorium-227 measurement arise from decay of Thorium-227. Calculations are based on measurement 77-80 days after separation.
***Actinium -227 levels are based on all thorium-227 arises from actinium-227. Calculations are based on measurements 77 days after separation. 92.5% ingrowth of thorium-227 from actinium-227 have occurred at this time.
****Actinium-227 level on the anion resin is calculated based on thorium-227 level measured 126 days after separation.

Loss of Actinium-227.

It is of most importance to reduce the loss of Actinium-227 in the process to a minimum. The amount of acinium-227 remaining on the anion exchange column has been calculated by measuring the thorium-227 level 126 days after separation. According to these measurements the amount of actinium-227 is around 3*10$^5$ Bq or 0.3 MBq remaining on the column. The loading on the column was 2500 MBq. Based on this figures the loss is around 0.012%. No significant amount of actinium-227 has been observed in other columns/solutions in the process.

Regeneration of Thorium-227.

Around 1.8*10$^6$ Bq thorium-227 was measured on the anion column after stripping. No other significant level of thorium-227 was measured on any other column or solutions. Based on this number, the regeneration of thorium-227 in the process will be over 99.5%.

Loss of Radium-223 in the Process.

According to the development of the process around 95% of radium-223 should be eluted from the first chromatographic step, the anion column. This yield is not possible to measure directly since remaining radium-223 on the anion column is washed back into the generator vial together with actinium-227 and thorium-227. It is possible to measure radium-223 content in all columns as well as the liquid fractions used in the process. In table 7 the different liquid fractions and columns have been measured. The losses of Radium-223 in the different steps are also calculated in % of total radium-223 produced.

Table 7 shows % radium-223 in the different fractions/columns at separation day. Results are calculated based on Germanium measurements day 13 after separation.

| Columns/fractions | Radium-223 compared to total amount of radium-223 in Drug Substance (%) |
|---|---|
| Anion column before wash with HCl | Not measured |
| Anion column after wash HCl | 0.000 |
| Small cation column 0.5 ml | 1.685 |
| Waste 1 | 0.000 |

Conclusion.

The loss of radium-223 in waste and on column is low. The major loss is on the small cation column as expected. The process is effective for producing radium-223 at high yield.

Measurement of the Second (Cation) Resin

It is possible to calculate the content of actinium-227 of the eluate from the 0.5 ml cation column. This calculation is based on the knowledge that the small cation column retains 750 Bq of actinium-227 of every 1 Bq actinium-227 which elutes. This ratio is around 750 for 30 ml 1.3M HNO$_3$.

After 77 days the % ingrowth of thorium-227 from actinium-227 is 92%. The amount of thorium-227 measured on the cation resin was less than 572 Bq. If all this thorium-227 arises from actinium-227 which is a worst case scenario, the maximum amount of actinium-227 on the column is:

$$572 \text{ Bq}/0.92 = 619 \text{ Bq actinium-227}$$

The total amount of actinium-227 in the 1100 MBq batch of radium-223 eluate from the cation exchange column will be:

Level of actinium-227 measured on column
Separation ratio of "retained" actinium-227/elueted actinium-227 the column:

$$619 \text{ Bq}/750 = 0.82 \text{ Bq.}$$

Final Purity of Drug Substance

Amount of radium-223 in drug substance: 1100 MBq
Amount of actinium-227 in eluate: 0.82 bq.
Bq actinium-227/MBq radium-223=0.82 Bq/1100 MBq=0.00075.
Specification: 45 Bq actinium-227 pr MBq radium-223: 45 bq/MBq
The specification is fulfilled by a factor of 45/0.00075=60000

The invention claimed is:

1. A method for the generation of $^{223}$Ra of pharmaceutically tolerable purity comprising
   i) preparing a generator mixture comprising $^{227}$Ac, $^{227}$Th and $^{223}$Ra;
   ii) loading said generator mixture onto a strong base anion exchange resin;
   iii) eluting said $^{223}$Ra from said strong base anion exchange resin using a first mineral acid in an alcoholic aqueous solution to give a first eluted $^{223}$Ra solution;
   iv) loading the $^{223}$Ra of the first eluted $^{223}$Ra solution onto a strong acid cation exchange resin; and
   v) eluting the $^{223}$Ra from said strong acid cation exchange resin using a second mineral acid in aqueous solution to provide a second eluted solution, wherein said $^{223}$Ra of pharmaceutically tolerable purity comprises less than 45Bq $^{227}$Ac per MBq $^{223}$Ra.

2. The method of claim 1 additionally comprising the step of:
   x) eluting said $^{227}$Ac and $^{227}$Th from said strong base anion exchange resin using a third mineral acid in aqueous solution, whereby to provide a mixture of $^{227}$Ac and $^{227}$Th, wherein step occurs at any time following step ii).

3. The method as claimed in claim 2 wherein at least 99.9% of the $^{227}$Ac loaded onto the resin in step ii) is recovered in step x).

4. The method as claimed in claim 3 wherein at least 98% of the $^{227}$Th loaded onto the resin in step ii) is recovered in step x).

5. The method of claim 1 additionally comprising the step of:
   y) storing said mixture of $^{227}$Ac and $^{227}$Th for a period sufficient to allow ingrowth of $^{223}$Ra by radioactive decay, whereby to regenerate a generator mixture comprising $^{227}$Ac, $^{227}$Th and $^{223}$Ra.

6. The method of claim 1 wherein the method purifies sufficient $^{223}$Ra for more than 10 typical doses.

7. The method of claim 1 wherein a $^{227}$Ac radioactivity of at least 500 MBq is employed in step i).

8. The method of claim 1 wherein the strong base anion exchange resin is a polystyrene/divinyl benzene copolymer based resin.

9. The method of claim 8 wherein said polystyrene/divinyl benzene copolymer based resin contains 1-95% DVB.

10. The method of claim 1 wherein the strong base anion exchange resin is an R—N$^+$Me$_3$ type (type I) resin or an R—N$^+$Me$_2$CH$_2$CH$_2$OH (Type II) resin.

11. The method of claim 1 wherein the first mineral acid is an acid selected from the group consisting of H$_2$SO$_4$ and HNO.

12. The method of claim 11 wherein the first mineral acid is HNO$_3$.

13. The method of claim 1 wherein the first mineral acid is used at a concentration of 0.01 to 5 M.

14. The method of claim 1 wherein the alcoholic aqueous solution comprises at least one alcohol selected from the group consisting of methanol, ethanol, and isopropanol.

15. The method of claim 14 wherein the alcoholic aqueous solution comprises methanol.

16. The method of claim 1 wherein the alcoholic aqueous solution comprises 20 to 99% methanol.

17. The method of claim 1 wherein the first eluted $^{223}$Ra solution has a contamination level of no more than 100 Bq $^{227}$Ac per 1 MBq $^{223}$Ra.

18. The method of claim 1 wherein the steps of loading the generator mixture onto the base anion exchange resin and eluting the first eluted $^{223}$Ra solution provide a separation ratio of $^{223}$Ra to $^{227}$AC of at least 10,000:1.

19. The method of claim 1 wherein the strong acid cation exchange resin is a polystyrene/divinyl benzene copolymer based resin.

20. The method of claim 19 wherein said polystyrene/divinyl benzene copolymer based resin contains 1-95% DVB.

21. The method of claim 1 wherein the strong acid cation exchange resin is of SO$_3$H type.

22. The method of claim 1 wherein the second mineral acid is an acid selected from the group consisting of H$_2$SO$_4$, HNO$_3$, and HCl.

23. The method of claim 22 wherein the second mineral acid is HNO$_3$.

24. The method claim 1 wherein the second mineral acid is used at a concentration of 0.5 to 5 M.

25. The method of claim 1 wherein the aqueous solution does not comprise any significant amount of an alcohol selected from the group consisting of methanol, ethanol, and isopropanol.

26. The method of claim 25 wherein the aqueous solution is substantially free of methanol.

27. The method of claim 1 wherein the second eluted solution has a contamination level of no more than 45 Bq $^{227}$Ac per 1 MBq $^{223}$Ra.

* * * * *

UNITED STATES PATENT AND TRADEMARK OFFICE
CERTIFICATE OF CORRECTION

PATENT NO. : 8,926,943 B2
APPLICATION NO. : 13/695353
DATED : January 6, 2015
INVENTOR(S) : Jan Roger Karlson et al.

Page 1 of 1

It is certified that error appears in the above-identified patent and that said Letters Patent is hereby corrected as shown below:

In the claims,

Column 19, Claim 11, Line 27, replace "HNO." with --$HNO_3$.--.

Signed and Sealed this
Fifth Day of May, 2015

Michelle K. Lee
*Director of the United States Patent and Trademark Office*